United States Patent [19]

Conti

[11] Patent Number: 4,972,721

[45] Date of Patent: Nov. 27, 1990

[54] DYNAMIC VASCULAR COMPLIANCE TESTER

[75] Inventor: James C. Conti, Galena, Mo.

[73] Assignee: Dynatek Laboratories, Inc., Galena, Mo.

[21] Appl. No.: 468,699

[22] Filed: Jan. 23, 1990

[51] Int. Cl.⁵ .............................................. G01N 3/00
[52] U.S. Cl. ...................................... 73/807; 73/37.5
[58] Field of Search ...................... 73/807, 37.5, 37.9, 73/798, 788, 789

[56] References Cited

FOREIGN PATENT DOCUMENTS 283524 9/1988 European Pat. Off. ............. 73/788

*Primary Examiner*—Jerry W. Myracle
*Attorney, Agent, or Firm*—Litman, McMahon & Brown

[57] ABSTRACT

A dynamic vascular compliance tester (change in radius with change in pressure) comprises an oscillatorily driven bellows to simulate pulsing a fluid pressure within a test specimen and a method of use thereof. The tester includes a high frequency pressure transducer and a pair of linear voltage-to-displacement transducers ("LVDT") providing outputs that are utilized cooperatively to determine the compliance of a test specimen. A first LVDT measures the volume of fluid in each pulse provided by the bellows and a second LVDT measures the change in length of the test specimen during the pulse. The tester also includes an offset drive mechanism that is operably adjustable such that the volume of fluid passing into the test specimen can be altered as desired.

11 Claims, 2 Drawing Sheets

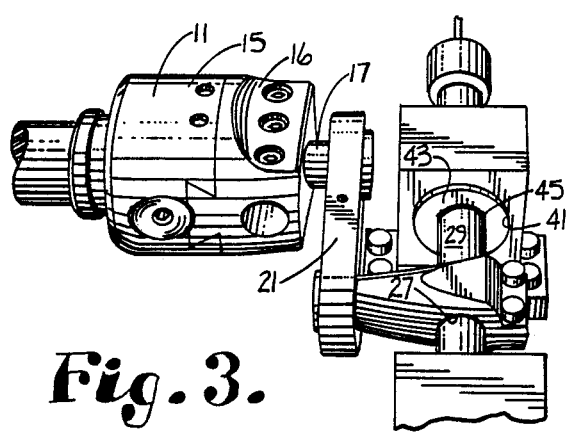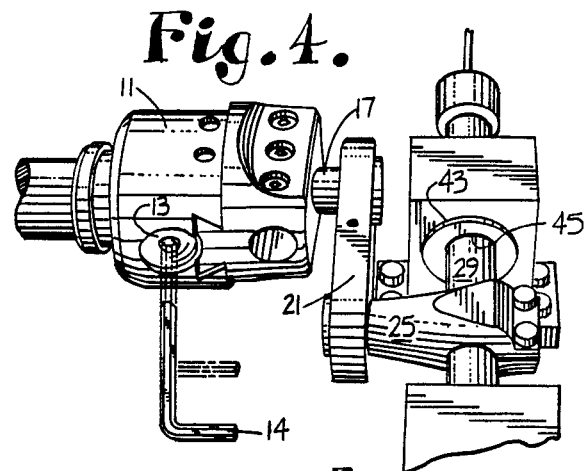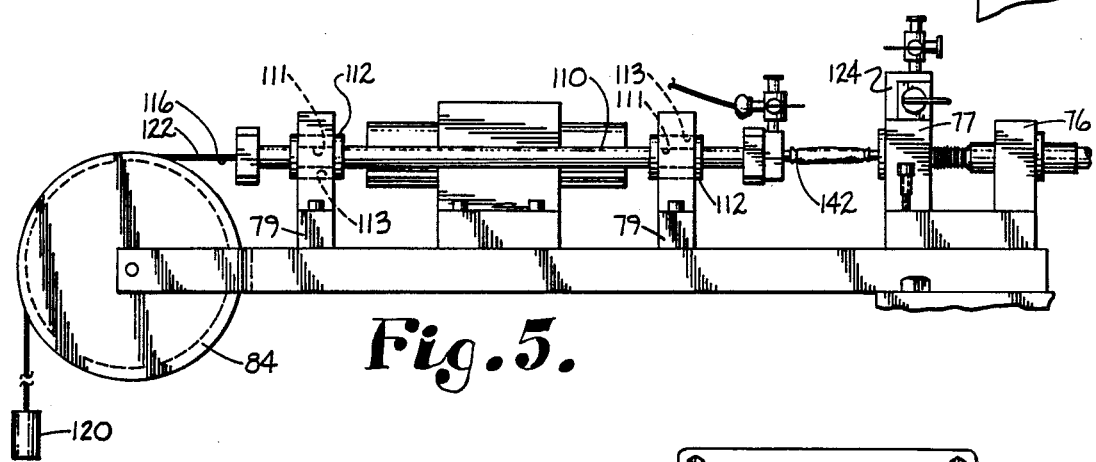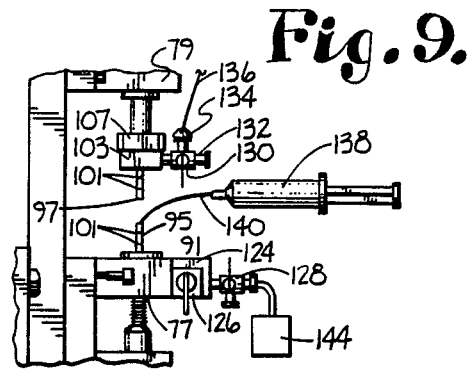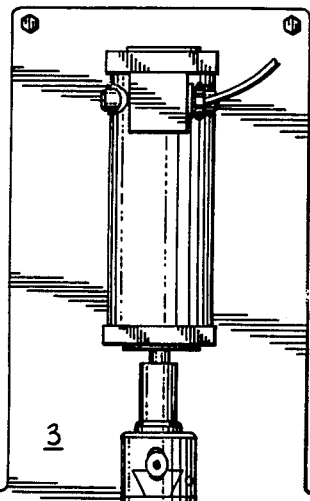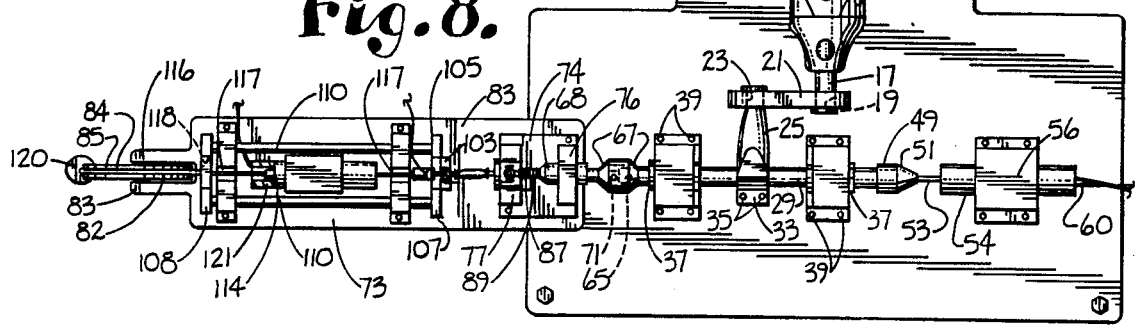

DYNAMIC VASCULAR COMPLIANCE TESTER

BACKGROUND OF THE INVENTION

The present application relates to a dynamic vascular compliance tester apparatus for determining vascular compliance of a vascular test specimen or an artificial graft for a vascular implant.

One of the most controversial areas in the field of vascular grafts has been the concept of compliance matching. The elastic properties or viscoelastic properties of tubular elements have been of interest for many years, particularly in the area of cardiovascular research. Medical research indicates that, when arteries and veins get stiff or lose their elasticity, they become very susceptible to atherosclerosis. In addition, if a compliance matching problem arises after the implantation of blood carrying vessels including artery or vein sections (both when removed from another portion of the body or when artificial), blood will sometimes deposit coagulation factors at the interface between the original vessel and the implanted vessel.

By determining the change in diameter or radius of the vessel and by simultaneously observing the pressure of the pulse which creates the change in radius of the vessel, a quantity commonly referred to as compliance can be calculated. For this type of testing, compliance is referred to as the percent change in radius which occurs when the corresponding blood pressure changes by the equivalent of 100 mm Hg pressure. (In actuality, blood pressure changes are somewhat less than 100 mm Hg but the results are extrapolated to provide an equivalent change in radius for the 100 mm Hg change in pressure for comparison purposes.)

During the past several years, various high-tech methods have been utilized in an attempt to measure the mechanical properties of arteries in vivo or in the body. The variety of methods which have been utilized are so fraught with complications and errors that those methods are almost useless. For example, one common technique used with arteries is to expose the vessel by surgically removing the surrounding tissue. A lever, which is connected to an electronic measuring instrument, is then placed against the outside wall of the artery. As the artery pulses, the lever is moved in proportion to the expansion and a measurement of the displacement of the lever is recorded. This technique has several flaws associated with it. In particular, when an artery is totally exposed to the air, it begins to constrict. Such a constricted vessel has lower elastic properties than those of a natural vessel. Further, the point where the lever touches the vessel becomes traumatized and does not respond to the varying blood pressure in the same manner that the remainder of the artery responds. As a result, erroneous data is obtained from this type of testing.

Another technique which has been attempted is an ultrasonic method whereby ultrasonic producing piezoelectric crystals are attached to the vessel. This approach has many of the same problems as those associated with the aforedescribed lever technique such as vessel exposure. In addition, the magnitude of the ultrasonic signal is functionally dependent upon the various angles involved with the topology of the sensor and the artery. As a result, any slight change in the critical angles can cause discrepancies in the resulting data obtained. Further, it is almost impossible to perfectly align the source of the ultrasound with the crystal because the position of the crystal usually shifts, however minutely, after surgical implantation thereof.

Another weakness of both of the foregoing techniques is that only the outside diameter of the vessel is measured; whereas, the dimension of the vessel which is of critical importance is the inside diameter. In addition to measuring the physical properties of actual vessels, it is desirable and beneficial to have a simple method of measuring the physical properties of synthetic vessels currently being developed.

It is also important to recognize that the physical properties of viscoelastic vessels normally change as the pulse frequency at which vessels are being tested changes. Specifically, many laboratory procedures utilize static techniques to measure the physical properties of tubing or vessels. When the same vessels are then used in situations where they are subjected to dynamic pressure changes, such as in a functioning artery, then the dynamic properties of those vessels may vary substantially from the measured static properties. The dynamic properties, which are the more important ones, may differ from those anticipated using static data.

SUMMARY OF THE INVENTION

A dynamic vascular compliance testing apparatus is provided which measures the radial or cross-sectional change in the inside wall, as opposed to the outside wall, of a test specimen such as a vascular implant or vessel, which results from pulsing a fluid under pressure into the implant or vessel. Application of the present invention eliminates the need to make arbitrary assumptions about the compressibility of the wall of the vessel which are otherwise necessary where the measurements are taken externally.

The apparatus includes a bellows to pump a known volume of fluid into the test specimen which causes an increased pressure in the specimen and alters the geometric configuration thereof. These changes are measured with two linear voltage-to-displacement transducers (hereinafter "LVDT"). The techniques utilized to monitor the cyclical fluid volume injected into the specimen by the compliance testing apparatus of the present invention are preferably accurate to better than one microliter per cycle. One of the LVDT's, which is spatially fixed relative to the bellows, measures the magnitude of the compression of the bellows which translates into the volume of fluid pulsed into the specimen. The other LVDT, which is mounted on a movable platen, measures the magnitude of the change in length of the test specimen when the fluid is injected therein.

By knowing the volume of the injected fluid and three physical measurements—the initial radius, the initial length, and the final length of the vessel—the resulting change in radius of the vessel, when the fluid is injected therein, can be calculated. With a known change in radius and a known change in pressure, the compliance of the test specimen, whether the specimen is a natural or a synthetic vessel, can be easily and directly calculated.

In addition to the foregoing, the compliance testing apparatus of the present invention measures the properties of these specimens at a variety of pumping frequencies. Under normal circumstances, the frequency range of biological importance basically lies between 50 and 200 cycles per minute; however, broader ranges can be tested, if necessary.

Another use for the compliance testing apparatus of the present invention, when operating at higher frequencies, is fatigue testing of elastic tubular elements. Prior to such fatigue testing, it is essential to know the maximum frequency at which the test can be performed. As the frequency at which the pressure pulse is delivered to an experimental vessel increases, the ability of the vessel wall to respond thereto becomes a limiting factor. As a result, the apparatus of the present invention can be used to determine the maximum frequency at which a tubular vessel can be tested under such accelerated conditions.

As aforementioned, the apparatus of the present invention is versatile and simple to use for measuring the dynamic vascular compliance of both synthetic grafts and biological vessels. In an actual application thereof, one end of a specimen is fluid-flow coupled to an extremely sensitive bellows which operatively delivers volumes accurate to within 1 microliter at pulse frequencies of 70–2000 cpm through the interior of the specimen. The opposite end of the specimen is fluid-flow coupled to a pressure transducer port on a movable platen. The platen is connected to an LVDT such that changes in length of the specimen can be measured. The platen is gravitationally tension loaded with a counter-balancing weight to assure geometric alignment. The measurements obtained therefrom provide the basis for the mathematical determinations of the compliance of the vessel specimen being tested.

An overall meritorious aspect of the present invention is that it provides a very simple method of evaluating such properties without the need for highly sophisticated computer equipment, complicated assumptions, or complex engineering equations.

OBJECTS OF THE INVENTION

Therefore, the objects of the present invention are: to provide an apparatus and a method for accurately measuring the properties related to the dynamic internal compliance of both synthetic grafts and both in vitro and in vivo biological vessels; to provide an apparatus which can be used to evaluate the compliance properties of such grafts or vessels at a variety of pulsing frequencies; to provide such an apparatus for evaluating fatigue resistance of various grafts fabricated from synthetic materials; to provide a method of using the apparatus to test compliance; and to generally provide an apparatus which is relatively easy to use, simple to maintain, easy to operate efficiently and reliably, and which generally performs the requirements of its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is an enlarged and fragmentary perspective view of the testing apparatus, taken along line 3—3 of FIG. 1.

FIG. 4 is an enlarged and fragmentary perspective view of the testing apparatus similar to that of FIG. 3 showing an adjustment wrench removed in solid lines and inserted to adjust in phantom.

FIG. 5 is an enlarged and fragmentary side elevational view of the testing apparatus similar to that of FIG. 2.

FIG. 8 is a top plan view of the tester apparatus with portions broken away to show details thereof.

FIG. 9 is an enlarged and fragmentary side elevational view of the testing apparatus including a syringe for injecting fluid into the apparatus.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
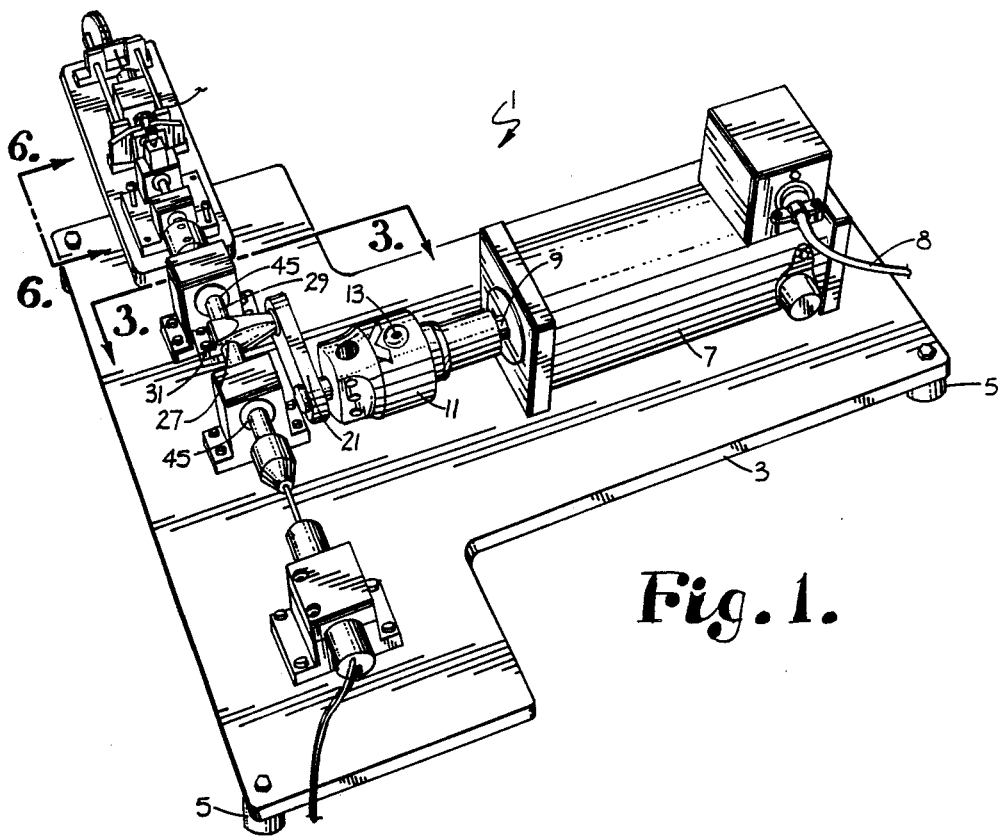
FIG. 1 is a perspective view of a dynamic vascular compliance testing apparatus in accordance with the present invention.

The reference numeral 1 generally refers to a dynamic vascular compliance testing apparatus in accordance with the present invention. The testing apparatus 1 is shown mounted on a platform 3 which, when operated in a horizontal orientation as shown in FIG. 1, is mounted on a plurality of resilient feet 5 to cushion and absorb mechanical oscillations and vibrations induced by the operation of the testing apparatus 1. The apparatus 1 may also be operated in a vertical orientation.

Mechanical power for driving the testing apparatus 1 is supplied by drive or motor means such as the illustrated variable speed electric motor 7. A suitable motor 7 is available from Dayton Corp., such as Model No. 4Z528. The motor 7 is removably rigidly secured to the platform 3. Electrical power for the motor 7 is supplied by a power cord 8 which is connectable to a conventional source of electrical energy (not shown).

The motor 7 includes a rotating shaft 9. Rigidly secured to the rotating shaft 9 is oscillating means for converting rotary motion to linear motion, such as the illustrated drive coupler 11, available as Model No. BT-2 boring head as manufactured by Bor-Thru. The coupler 11 has a rotating tightening and adjustment mechanism or adjuster 13 which is adapted to receive and be adjusted by an Allen wrench 14 which permits altering the eccentricity of the drive coupler 11. For comparison purposes, FIG. 3 shows the coupler 11 in a neutral, non-eccentric configuration, whereas FIG. 4 shows the coupler 11 adjusted to an eccentric configuration. In particular, the coupler includes a pair of heads 15 and 16 which slide radially with respect to each other and perpendicular to a common axis thereof when the adjuster 13 is loosened.

Extending from the distal end of the coupler 11 is a cylindrically shaped shaft 17 which is rotatably and pivotally secured in a first throughbore 19 of a crank arm 21. Rotatably and pivotally secured in a second throughbore 23 of the arm 21 is a drive shaft 25 which has a lateral throughbore 27 with a diameter dimensioned slightly greater than a diameter of a drive rod 29 inserted therethrough. The drive shaft 25 is rigidly secured to the drive rod 29 by clamping means, such as a slot 31 which communicates the throughbore 27 with a distal end 33 of the drive shaft 25 such that clamping bolts 35 traversing the slot 31 can be threadedly advanced to rigidly secure the drive shaft 25 about the drive rod 29.

Two bearing blocks 37 are rigidly secured to the platform 3 by a plurality of bolts 39. A throughbore 41 through each block 37 has a diameter dimensioned slightly greater than an outer diameter of a bushing 43. The bushings 43 each have an axial throughbore 45 which is dimensioned slightly greater than the diameter of the drive rod 29 such that the drive rod may undergo uninhibited longitudinal oscillatory or reciprocating movement therein as hereinafter described.

Figure 2:
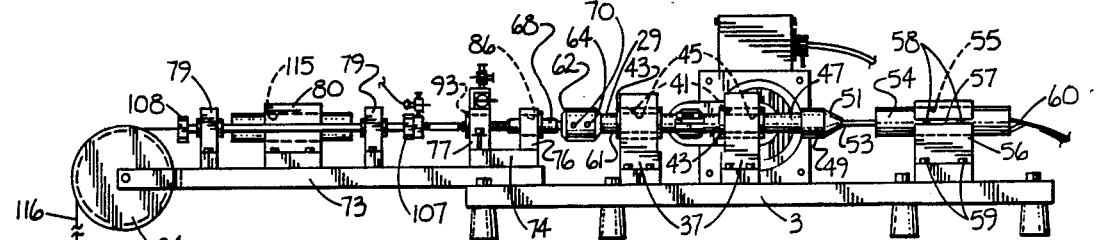
FIG. 2 is a side elevational view of the vascular compliance testing apparatus.

As seen in FIG. 2, a right end 47 of the drive rod 29 is rigidly secured to an adapter 49. A distal end 51 of the adapter 49, which is substantially conically shaped, is rigidly secured to displacement measuring means, such as a core rod 53 which, in turn, communicates with a linear voltage-to-displacement transducer 54 ("LVDT"), that is inserted in a throughbore 55 of a bracket 56. The LVDT 54 is rigidly secured relative to the bracket 56 by clamping means, including a radial slot 57 communicating with the bore 55 such that bolts 58 can be threadedly advanced therethrough to rigidly secure the bracket 56 about the LVDT 54. The bracket 56, in turn, is rigidly secured to the platform 3 with a plurality of bolts 59. Cables 60 electronically communicate the signals generated by the LVDT 54 to external monitoring equipment (not shown). The core 53 and the LVDT 54 are readily available; for example, Model No. 0242-0000 as manufactured by Trans-Tek.

A left end 61 of the drive rod 29, as shown in FIG. 2, is rigidly secured to a bellows drive coupling 62, by a radially extending setscrew 64 which is threadedly advanced to contact the left end 61 (FIG. 8) of the drive rod 29 inserted in an axial partial bore 65 of the coupling 62. The drive coupling 62 is constructed of any suitable material, such as aluminum with a clear anodized finish. The drive coupling 62 has circumferential chamfers 67 at the axial ends thereof.

Similarly secured to the opposite axial end of the coupling 62 is a bellows drive pin 68. The drive pin 68 is constructed of phenolic or other suitable material. One end of the drive pin 68 is adapted for removable rigid securement to the coupling 62, such as with a setscrew 70 radially communicating with an axial partial bore 71 in the coupling 62.

Rigidly secured to the platform 3 is a plate 73. Rigidly secured to the plate 73 is a bellows bracket 74 having two upright standards 76 and 77, two platen brackets 79 and a LVDT bracket 80. Stabilizing means, such as a pulley 84, is utilized to physically stabilize the present invention during a utilization thereof. Pivotally and rotatably mounted in a slot 82 at a distal end 83 of the plate 73 is the pulley 84 with a groove 85 in the circumferential periphery thereof.

A throughbore 86 in the rightmost standard 76 of the bellows bracket 74, as shown in FIG. 2, is dimensioned such that the bellows drive pin 68 slides uninhibitedly axially therein. Fluid supply means, pumping means or pulsing means such as the illustrated bellows 89, supply working fluid, as described below. The bellows 89 is secured by gluing, threaded connection or the like to a distal end 87 of the drive pin 83, with an inner chamber 90 which is constructed of nickel alloy or other suitable material. (A suitable bellows is available as Model No. FC1 from Servometer.) A bushing 91 is inserted into and rigidly secured in a throughbore 93 of the leftmost standard 77 of the bellows bracket 74 wherein the throughbore 93 is dimensioned greater than the maximum diameter of the bellows 89. A distal end of the bellows 89 is rigidly secured in fluid communication with the bushing 91.

Removably rigidly secured to an axial throughbore (not shown) of the bushing 91 is specimen support means, such as illustrated tubes or connectors 95 and 97, which are constructed of Series 300 stainless steel or other suitable material. The connectors 95 and 97 are substantially cylindrically shaped, with an outside diameter dimensioned to be slidably insertable into an artery, vessel or specimen 99 for testing. The connector 95 is hollow such that it communicates with the bellows chamber 90 through the bushing 91. In one application of the present invention 1, the connector 95 has an outside diameter of approximately 1/6 inch, an inside diameter of 0.135 inches, and a length of ½ inch. A plurality of different size connectors (not shown) are normally provided with the apparatus 1 having an assortment of outside diameters to allow interchangeability for adapting the apparatus 1 to accommodate the diameter of various sizes of test specimens. One or more grooves 101 about the circumferential periphery of the connectors 95 and 97 provide securement means for securing the specimen 99 to the connectors 95 and 97.

The specimen connector 97, which is substantially identical to the connector 95, is spaced axially from the connector 95 such that the specimen 99 can be positioned for evaluation therebetween. The connector 97 is removably rigidly secured to a bushing 103, which, in turn, is rigidly secured to a platen 105. The platen 105 has two end sections 107 and 108 which are rigidly connected to each other with a pair of parallel bars or rods 110. Each of the rods 110 is mounted in a pair of coaxial bores 111 through bushings 112 which, in turn, are mounted in a pair of coaxial throughbores 113 in the brackets 79 such that the rods 110 can uninhibitedly oscillate axially therein. Alternatively, the rods 110 may be mounted directly in throughbores in the brackets 79 such that the need for the bushings may be eliminated.

Measuring means is operably adapted to measure the differential changes in length of the specimen 99, such as an LVDT 114. In that case, the LVDT 114 has a hollow center and is securely clamped in a throughbore 115 in the bracket 80, by a clamp mechanism which comprises a radial slot communicating with the bore 115 as hereinbefore described for securing the LVDT 54 within the bracket 56.

A cable 116 is rigidly secured to the platen end 107. The cable 116 is passed through slots 117 of the platen brackets 79, the hollow center of the LVDT 114, a throughbore 118 of left platen end section 108 and over the pulley 84 where the cable 116 is secured to a weight 120. A position core 121 is placed about and secured to the cord 116 where it passes through the LVDT 114.

The LVDT 54 is substantially co-axial with the core 53, the adapter 49, the drive rod 29, the bellows drive coupling 62, the bellows drive pin 68, the bellows 89, the connectors 95 and 97, an upper tangential portion 122 of the cable 116, the LVDT 114 and the core 121.

Secured to the bellows bracket standard 77 with a valve clamp 124 is a valve 126, available as Model No. HV1-1/86725, manufactured by Hamilton. Attached to the valve 126 is a stopcock 128. The standard 77 is adapted to communicate the stopcock 128 and the valve 126 with the bellows chamber 90.

Secured to the bushing 103 is a three-way stopcock 130, with one port thereof serving as a bleeder port 132 and another port thereof adapted to interface with pressure measuring means, such as a high frequency response pressure transducer 134, available as Model No. 8510B-5, manufactured by Endevco. Conductors 136 communicate the output from the pressure transducer 134 to auxilliary monitoring equipment (not shown).

In preparation for use of the present invention 1, the inside diameter of the test specimen 99 is measured, such as by the insertion of standard machinist's pin inserts into the ends thereof or the like. The connectors 95 and 97 having appropriately dimensioned diameters are then secured to the bushings 91 and 103. The initial effective working length of the specimen 99 is then determined by measuring the displacement between the opposing ends of the connectors 95 and 97.

The dynamic vascular compliance tester apparatus 1 is then oriented vertically with the pulley 84 spaced substantially above the bellows 89 (that is, rotated 90° about the right hand corner as seen in FIG. 2). The chamber 90 contained within the bellow 89, the bushing 91 and the connector 95 are substantialy filled with a working fluid 137, such as distilled water, saline solution or other suitable liquid. Any suitable fluid supply means may be utilized to furnish and inject the working fluid 137 therein; for example, a syringe 138 connected to a length of flexible tubing 140, such as tubing constructed of polyethylene or the like, as illustrated in FIG. 9. In order to fill the chamber 90 with the working fluid 137 with the syringe 138, the distal end of the syringe tube 140 is inserted through the connector 95 and extended directly into the bellows chamber 90. The chamber 90 is then filled by ejecting the fluid 137 from the syringe 138 through the tubing 140.

The test specimen 99 is then telescoped over the opposing ends of the graft connectors 95 and 97 such that the specimen 99 extends over and encompasses at least one of the circumferential grooves 101 on each of the connectors 95 and 97. The ends of the specimen 99 are secured on the connectors 95 and 97 by suitable means, such as by clamping or by securing with sutures 142 snugged around the specimen 99 in cooperation with the grooves 101 or the like. The cable 116 is then entrained over the pulley 84 and secured to the weight 120.

The magnitude of the weight 120 is appropriately selected to provide a desired amount of tension axially along the specimen 99. The minimum magnitude permissible for the weight 120 is slightly greater than (a) the weight of the moving components between the specimen 99 and the pulley 85, plus (b) any frictional forces which must be overcome in order to return such movable components to their uppermost positions (when the apparatus 1 is operated in a vertical orientation) between pulses.

The maximum magnitude permissible for the weight 120 is dependent on the characteristics of the specimen 99 and is limited so that destructive deformation of the specimen 99 is avoided. Application of excessive tension becomes experimentally apparent whenever successive indentically injected volumes (as hereinafter described) yield inconsistent results.

The wrench 14, after insertion into the adjuster 13, is turned clockwise or counterclockwise until the desired relative quantity of fluid 137 will be injected into the specimen 99 during operation of the apparatus 1, when the bellows 89 are at peak compression of the oscillatory cycle. As the bellows 89 are cycled, the core 53 is similarly moved axially relative to the LVDT 55. Thus, the actual displacement of the bellows 89 from peak compression to peak distension, and the resulting volume of fluid 137 pulsed into the specimen 99, is determinable from the signal generated by the LVDT 55. By previously calibrating the change in volume of the bellows 89 as a function of change in axial length of the bellows 89, the amount of fluid 137 pulsed from the bellows 89 into the specimen 99 is controlled by the eccentricity adjustment of the drive coupler 11.

The stopcock 130 is then adjusted to partially open the bleeder port 132. A source 144 of the working fluid 137 is then attached to the stopcock 128 and the stopcock 128 is accordingly adjusted such that the working fluid 137 can be forced through the stopcock 128 until all communicating cavities including the cavities within the bellows 89, the connectors 95 and 97, the pressure transducer 134, and the stopcocks 128 and 130 such that all air bubbles are effectively bled from the lumen of the specimen 99 and all internal cavities communicating therewith.

Figure 6:
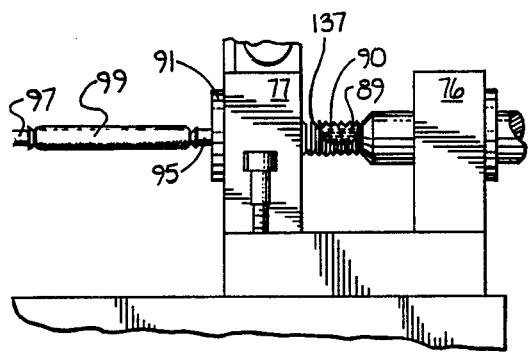
FIG. 6 is an enlarged and fragmentary side elevational view of the testing apparatus, taken along line 6—6 of FIG. 1, showing a bellows thereof expanded with portions broken away to show details thereof.
Figure 7:
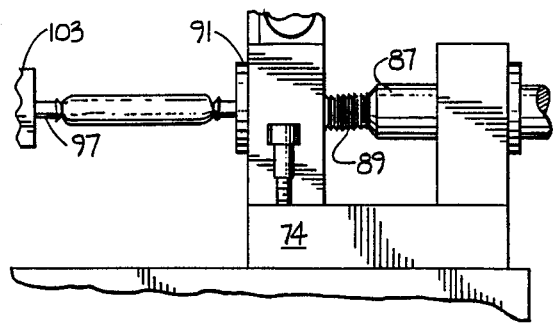
FIG. 7 is an enlarged and fragmentary side elevational view of the testing apparatus similar to that of FIG. 6, showing the bellows compressed.

Sufficient fluid is injected into the specimen 99 while the bellows 89 are in its distended or pulse-rest configuration as shown in FIG. 6, such that the specimen 99 is filled but not inflated. The displacement of the drive shaft 25 relative to that of the drive rod 29 is adjusted such that the bellows 89 are partially compressed at the distended configuration. As an example, the bellows 89 are compressed approximately ten percent of total design compression at pulse rest. It is important that the physical characteristics of the bellows 89 be taken into account when locating the various components relative to each other so the bellows 89 are not over-compressed or over-extended beyond design limits.

After each test run with a particular specimen 99, further manipulation of the adjuster 13 with the wrench 14 alters the quantity of the fluid 137 pulsed into the specimen 99 such that greater or lesser pressure is applied to the specimen 99 for further evaluation of vascular compliance as a function of pressure. As the specimen 99 inflates with the injected working fluid 137, the specimen 99 expands laterally outward in order to contain the increased volume. Simultaneously, the length of the specimen 99 may also vary (normally lengthening).

As a result of any variation in length of the specimen 99, the platen 105 with the cable 116 and the weight 120 connected thereto, is physically shifted accordingly. The displacement of the platen 105, which is substantially identical to the change in length of the specimen 99 resulting from the injected pulse of fluid 137, is determined by the signal generated by the LVDT 114 due to the axial movement of the core 121 attached to the cable 116 which passes through the center of the LVDT 114.

As a result, the change in length of the specimen 99 between the connectors 95 and 97 required to contain the quantity of fluid 137 pumped therein during the pulse, as measured by the output of the LVTD 114, translates into an experimentally determined inner radius of the specimen 99 at the pulse peak. Thus, from the measurements of the initial length of the specimen 99 between the connectors 95 and 97, any change in the length of the specimen 99 as determined from the output of the LVDT 114, and the initial radius of the specimen 99, the final radius of the specimen 99 as a function of pressure (as indicated by the output of the pressure transducer 134), or the compliance of the specimen 99, can be determined. The final calculations are customarily mathematically extrapolated to a pressure of 100 mm Hg to permit equivalent comparisons among different specimens.

Experience has demonstrated that gradually increasing the weight 120 in coordination with manipulation of the adjuster 13 permits the operator of the apparatus 1 to determine a maximum reproducible radial deflection of the specimen 99 for a maximum volume of the working fluid 137 pulsed by the bellows 89 into the specimen 99 without destructively deforming the specimen 99.

The apparatus 1 of the present invention can also be utilized to ascertain dependency of the specimen 99 upon pulse frequency. To change the simulated pulse rate, the rotational rate of the variable speed motor 7 is varied accordingly.

Another aspect of the application of the present invention 1 is the ascertainment of potential solution or temperature sensitivities for any particular compliance determination. A specimen 99 is first preliminarily tested at room temperature followed by a similar test at an elevated temperature, such as at normal body temperature of 37° C. If the variance of the results obtained from the two comparison tests is within acceptable limits, the actual determination is conducted at room temperature. Otherwise, the actual determination is conducted at the elevated temperature to more closely assimilate an in vivo environment.

It is to be understood that while certain forms of the present invention have been illustrated and described herein, it is not to be limited to the specific forms or arrangement of parts described and shown.

What is claimed and desired to be secured by Letters Patent is as follows:

1. A compliance testing apparatus for determining the compliance of both artificial and natural blood vessel graft specimens having an internal lumen; said apparatus comprising:
    (a) fluid supply means for flow communicating with the lumen of the specimen and adapted to inject fluid under pressure into the lumen; and
    (b) measuring means for determining an internal radius of the lumen for at least one selected fluid pressure within the lumen.

2. The apparatus according to claim 1 wherein said apparatus includes:
    (a) oscillating means cooperating with said fluid supply means to oscillate fluid within the lumen while said measuring means determines the radius of the lumen.

3. The apparatus according to claim 1 wherein:
    (a) said measuring means comprises a differential axial length measuring mechanism to determine the axial variation in length of a specimen when a selected fluid volume under a selected pressure is injected into the specimen; and
    (b) a fluid volume measuring mechanism for determining the selected volume of fluid.

4. A compliance testing apparatus for evaluating compliance of a tubular specimen, said apparatus comprising:
    (a) pumping means for injection of a fluid into said specimen;
    (b) a first measuring means for determining a volume of said injected fluid;
    (c) a second measuring means for determining axial length variation in said specimen resulting from said injection; and
    (d) pressure measuring means for determining pressure of said fluid in said specimen.

5. The testing apparatus according to claim 4 wherein:
    (a) said pumping means is an oscillatorily driven bellows.

6. The testing apparatus according to claim 5 wherein:
    (a) said oscillatory motion is provided by an eccentricity adapter driven by a motor.

7. The testing apparatus according to claim 4 wherein:
    (a) said first measuring means is a linear voltage-to-displacement transducer system.

8. The testing apparatus according to claim 7 wherein:
    (a) said second measuring means is another linear voltage-to-displacement transducer system.

9. The testing apparatus according to claim 4 wherein:
    (a) said pressure measuring means is a high frequency response pressure transducer.

10. A testing apparatus for dynamically evaluating pressure-volume dependency of a vascular specimen, said apparatus comprising:
    (a) support means for supporting the specimen;
    (b) securement means for mounting a specimen with respect to said support means; said specimen cooperatively connected to a movable platen to allow for dynamic variations in length of said specimen;
    (c) pulsing means for periodically pulsing fluid into said specimen; said pulsing means comprising a bellows wherein said bellows is subjected to oscillatory axial distensive and compressive motion;
    (d) drive means for providing said oscillatory motion; said drive means powered by a variable speed electric motor cooperating with an eccentric drive shaft adapter;
    (e) first displacement measuring means comprising a first linear voltage-to-displacement transducer for determining an axial displacement of said oscillatory motion of said bellows, so as to allow determination of fluid-flow volume into the specimen;
    (f) second displacement measuring means comprising a second linear voltage-to-displacement transducer for determining a dynamic variation in length of said specimen during said oscillatory motion; and
    (g) stabilizing means for operably maintaining geometric alignment and placement of said specimen and said movable platen; said stabilizing means consisting of a weighted cable entrained over a pulley.

11. The testing apparatus according to claim 10 wherein:
    (a) said apparatus can operably assimilate pulse rates up to approximately 2,000 pulses per minute.

* * * * *